United States Patent [19]
Shih et al.

[11] Patent Number: 5,006,206
[45] Date of Patent: Apr. 9, 1991

[54] PROPYLENE OXIDE PURIFICATION

[75] Inventors: T. Thomas Shih, Bryn Mawr; William J. Sim, Newtown Square, both of Pa.

[73] Assignee: Arco Chemical Technology, Inc., Wilmington, Del.

[21] Appl. No.: 491,872

[22] Filed: Mar. 12, 1990

[51] Int. Cl.$^5$ .................. B01D 3/40; C07D 301/32
[52] U.S. Cl. .............................. 203/55; 203/56; 203/63; 549/541; 549/542
[58] Field of Search .............. 203/55, 53, 56, 63, 203/14; 549/541, 542

[56] References Cited
U.S. PATENT DOCUMENTS

| | | | |
|---|---|---|---|
| 3,449,219 | 6/1969 | Schmidt | 549/541 |
| 3,480,519 | 11/1969 | Nelson et al. | 549/541 |
| 3,632,482 | 1/1972 | Hoory et al. | 549/541 |
| 3,838,020 | 9/1974 | Kageyama et al. | 549/541 |
| 4,140,588 | 2/1979 | Schmidt | 203/92 |
| 4,304,639 | 12/1981 | Hardy et al. | 549/541 |
| 4,402,794 | 9/1983 | Nemet-Mavrodin et al. | 549/541 |

FOREIGN PATENT DOCUMENTS 0118873 3/1976 German Democratic Rep. .

OTHER PUBLICATIONS

Weissberger, "Distillation", Technique of Organic Chemistry, vol. IV, 2nd ed., 468-469 & 508.

*Primary Examiner*—Virginia Manoharan
*Attorney, Agent, or Firm*—William C. Long

[57] ABSTRACT

A method is provided for the separation by extractive distillation of hydrocarbon impurities from propylene oxide wherein t-butyl alcohol/water is used as extractive distillation solvent.

3 Claims, 1 Drawing Sheet

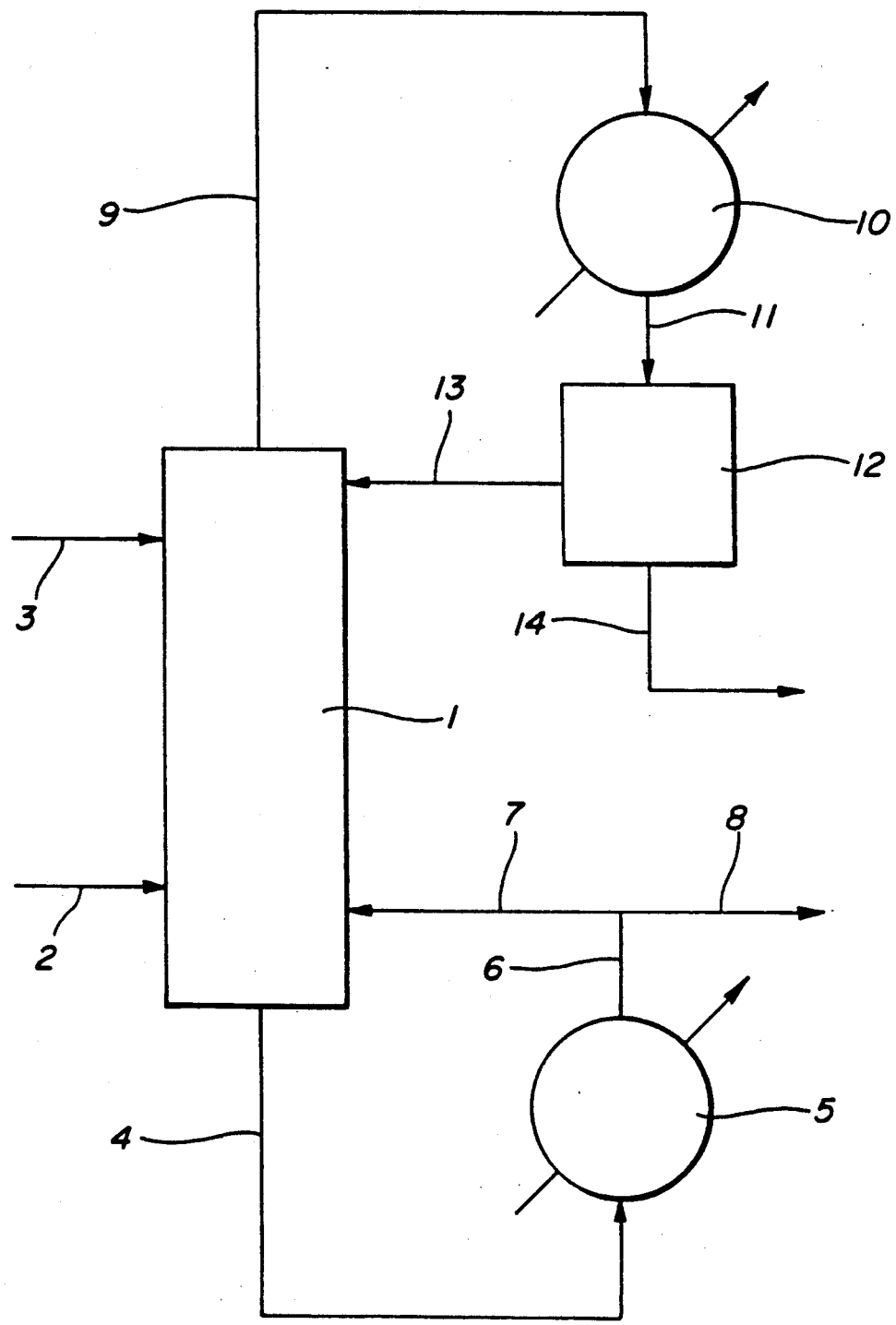

PROPYLENE OXIDE PURIFICATION

BACKGROUND OF THE INVENTION

1. Field of the Invention

The present invention relates to the separation of hydrocarbon impurities from lower alkylene oxides such as propylene oxide by extractive distillation with a t-butyl alcohol/water solvent.

2. Description of the Prior Art

Monoepoxides such as propylene oxide are highly important chemicals useful in a great number of applications. An important commercial technology for producing the monoepoxides is via the catalytic reaction between the corresponding olefin and an organic hydroperoxide. See, for example, U.S. Pat. No. 3,351,635.

In carrying out this reaction the organic hydroperoxide is reduced to the corresponding alcohol Also produced, however, are small amounts of other oxygen-containing compounds such as methanol, acetone, acetaldehyde and the like, as well as hydrocarbons which are difficult to separate. In general, the alcohol resulting from the reduction of the hydroperoxide can be separated from the epoxide product by ordinary distillation methods, particularly since the organic hydroperoxide employed can be selected to permit this separation. The small amounts of hydrocarbons and other oxygenated compounds, however, remain as impurities in the olefin oxide product. For certain of the epoxides, it is extremely important that these impurities be reduced to a very low p.p.m. level, e.g. below 50 ppm.

Hydrocarbon impurities associated with the lower alkylene oxides are paraffinic and olefinic hydrocarbons and in the case of propylene oxide are believed to be propylene derivatives having from 4 to 7 carbon atoms per molecule, especially derivatives having 6 carbon atoms per molecule The $C_6$ compounds include primarily methyl pentenes and methyl pentanes. These materials have boiling points sufficiently close to that of propylene oxide (about 35° C. at 760 mm/Hg) so that they are not effectively separated from propylene oxide by direct fractionation. In some cases an azeotrope is formed, making separation even more difficult.

U.S. Pat. No. 3,843,488 describes the separation of contaminating hydrocarbons from propylene oxide by distillation in the presence of a $C_8$ to $C_{20}$ alkane, alkene or naphthene. U.S. Pat. No. 3,909,366 describes the separation of contaminating hydrocarbons from propylene oxide by distillation in the presence of aromatic hydrocarbons having 6 to 12 carbon atoms. U.S. Pat. No. 3,464,897 shows propylene oxide purification by extractive distillation with aliphatic or cyclic paraffins having 8 to 12 carbon atoms.

It has previously been proposed to separate oxygen-containing impurities from the propylene oxide by extractive distillation using lower glycols such as ethylene glycol and propylene glycol. See U.S. Pat. No. 3,578,568 which describes this procedure and which teaches use of solvent in amount to comprise 15 to 50% of the vapor space in the distillation zone. Copending application Ser. No. 07/327,876 filed Mar. 17, 1989 describes a similar separation but one which uses much lower solvent concentrations whereby propylene oxide losses are reduced. U.S. Pat. No. 4,140,588 shows the use of water as extractive distillation solvent to separate oxygenated impurities from propylene oxide. East German Patent 118,873 shows the use of alcohol such as t-butyl alcohol to separate oxygenated impurities from propylene oxide.

BRIEF DESCRIPTION OF THE INVENTION

In accordance with the present invention, it has been found that lower alkylene oxides having 2 to 4 carbon atoms, particularly propylene oxide, containing hydrocarbon impurities can be purified by extractive distillation using t-butyl alcohol/water as extractive distillation solvent.

BRIEF DESCRIPTION OF THE DRAWINGS

The accompanying drawing illustrates the invention.

DETAILED DESCRIPTION OF THE INVENTION

This invention is applicable to the purification of propylene oxide prepared, for example, by reaction of an organic hydroperoxide with propylene and containing $C_4$ to $C_7$ hydrocarbon contaminants, generally in amounts of 100 to 3000 ppm by weight, usually 200 to 1000 ppm.

As has been pointed out, in the preparation of $C_2$–$C_4$ alkylene oxides such as propylene oxide various impurities are formed including $C_4$–$C_7$ hydrocarbons as well as oxygencontaining materials such as water, low molecular weight alcohols, low molecular weight ketones, low molecular weight aldehydes and the like. In accordance with this invention, the impure alkylene oxide is subjected to extractive distillation with t-butyl alcohol/water extractive solvent whereby hydrocarbon impurities are separated overhead as lights from the alkylene oxide and solvent mixture. Oxygenated impurities such as acetaldehyde and methyl formate are also separated as overhead lights. Thereafter, oxygenated impurities such as methanol can be separated by the procedure of said copending application Ser. No. 07/327,876 filed Mar. 17, 1989, for example The solvent mixture used in the extractive distillation comprises a mixture of about 2–50 wt.% water with t-butyl alcohol, preferably 5–30 wt.% water with t-butyl alcohol and most preferably 10–20 wt.% water with t-butyl alcohol. Although certain oxygenated impurities can be separated using t-butyl alcohol extractive solvent alone, as shown in East German Patent 118,873, water must also be included in the solvent mixture in order to separate hydrocarbon impurities according to this invention.

The method of this invention can be carried out either in a batch system or a continuous system. In the batch system the impure alkylene oxide, e.g., propylene oxide, is introduced into a vessel which can be heated and which is fitted with a fractionation column into which the extractive solvent can be introduced. The extractive solvent is introduced into the fractionating column at a point near the top of the column so that preferably there is some fractionation above the point of introduction. Reflux is also provided. The extractive solvent is suitably introduced at a temperature approximately the same as the boiling point of the mixture in the vessel at the point of introduction.

In the batch process the impure alkylene oxide mixture is heated to boiling and the solvent is introduced into the column in the appropriate amount. Hydrocarbon impurities are withdrawn overhead from the column while the solvent and alkylene oxide, together with any contained oxygenated impurities, accumulate in the distillation vessel until finally all of the hydrocarbons or substantially all have been distilled overhead Reflux to feed ratios of about 0.2:1 to 5:1 generally are appropriate.

In the continuous system the feed consisting of the impure alkylene oxide mixture is introduced into a fractionation tower near the middle or lower section of the tower and the t-butyl alcohol/water extractive solvent is introduced into the upper section of the tower. The bottom of the tower is generally provided with a reboiler system to provide the necessary heat for fractionation. The bottoms from the tower consisting of the solvent and alkylene oxide as well as impurities such as methanol passes through the reboiler where it is heated by indirect exchange or by direct heat and a portion of the bottoms liquid thus heated and partially vaporized is recycled to the lower part of the column. The remaining portion is withdrawn. The overhead vapors consisting of the hydrocarbon impurities are withdrawn from the tower and condensed. Usually in accordance with conventional practice a portion of the condensate is returned as recycle or reflux to the top of the tower. Reflux to feed ratios of about 0.2:1 to 5:1 are likewise appropriate. Such a system is well known in accordance with conventional engineering practices in extractive distillation processes and many modifications thereof are known and can be employed.

One embodiment of the foregoing description of the continuous system is shown in the drawing wherein numeral 1 refers to the fractionation tower or extractive distillation zone which is provided with conventional trays, packing or the like. The impure propylene oxide mixture is introduced into tower 1 through line 2, and the extractive solvent is introduced into tower 1 through line 3. The bottoms from the tower comprised of the propylene oxide and the solvent is removed through line 4 and passed through reboiler 5 wherein the bottoms are heated. Heated liquid is passed through line 6 and a portion is returned through line 7 to the tower 1 to provide the heat necessary for the distillation. The remaining portion of the bottoms is removed through line 8 and appropriately passed to a stripper (not shown) wherein purified propylene oxide is stripped overhead from a bottoms solvent stream which is recycled. The overhead vapors consisting of the hydrocarbon impurities as well as acetaldehyde and methyl formate are withdrawn from the tower through line 9 and passed to condenser 10 and from condenser 10 through line 11 to receiver 12. A portion of the condensate can be returned to the top of the tower 1 through line 13, as reflux, and the remainder of the condensate is withdrawn from the receiver 12 through line 14.

The following example is provided to illustrate the invention in greater detail and to demonstrate its utility. It will be understood, however, that the invention is not to be construed as being limited thereto.

EXAMPLE 1

A continuous extractive distillation run was carried out in a ninety-five (95) tray two-inch Oldershaw column with the solvent feed and propylene oxide feed at 10 and 65 trays from the top, respectively. The column was operated at 1 atmospheric pressure About 623 grams/hr of propylene oxide containing about 200 ppm $C_7$ hydrocarbon impurities, 1200 ppm $C_4$–$C_5$ hydrocarbon impurities, 500 ppm $C_6$ hydrocarbon impurities, 400 ppm acetaldehyde and 100 ppm methyl formate were fed to the distillation column at 65th tray from the top while solvent comprised of 17 wt.% water and 83 wt.% t-butyl alcohol was fed to the 10th tray from the top at the rate of 934 grams/hr, a solvent to feed ratio of 1.5. About 1544 grams/hr of purified propylene oxide and solvent were separated as bottoms while about 13 grams/hr of overhead were removed. The column reflux to feed ratio was 1:1, overhead temperature was 49° C. and bottoms temperature was 72° C.

The overhead stream was comprised by weight of about 90% propylene oxide, 6% $C_4$–$C_5$ hydrocarbons, 1.5% $C_6$ hydrocarbons, 350 ppm $C_7$ hydrocarbons, 0.9% methyl formate and 1.5% acetaldehyde.

The bottoms stream was passed to a stripping column and a purified propylene oxide stream recovered overhead from a bottoms solvent stream which was recycled. The purified propylene oxide product contained 6 ppm methyl formate and 10 ppm $C_7$ hydrocarbon and no detectable amounts of methyl formate, $C_4$–$C_5$ hydrocarbon or $C_6$ hydrocarbon.

What is claimed is:

1. An extractive distillation process for the separation of hydrocarbon impurities from propylene oxide which consists essentially introducing a feed comprises of propylene oxide containing hydrocarbon impurities into an intermediate section of an extractive distillation zone, introducing extractive distillation solvent consisting essentially of a mixture of about 2–50 wt.% water with t-butyl alcohol into the upper section of said extractive distillation zone, distilling said hydrocarbon impurities overhead from said extractive distillation zone and removing a mixture consisting essentially of said extractive distillation solvent and said propylene oxide substantially free of said hydrocarbon impurities from the lower section of the said extractive distillation zone.

2. The method of claim 1 wherein said extractive distillation solvent consists essentially of 5–30 wt.% water.

3. The method of claim 1 wherein said extractive distillation solvent consists essentially of 10–20 wt.% water.

* * * * *